(12) United States Patent
Van Berge et al.

(10) Patent No.: US 7,375,055 B2
(45) Date of Patent: May 20, 2008

(54) COBALT CATALYSTS

(75) Inventors: Peter Jacobus Van Berge, Sasolburg (ZA); Jan Van De Loosdrecht, Sasolburg (ZA); Jacobus Lucas Visagie, Sasolburg (ZA)

(73) Assignee: Sasol Technology (Proprietary Limited), Johannesburg (ZA)

( * ) Notice: Subject to any disclaimer, the term of this patent is extended or adjusted under 35 U.S.C. 154(b) by 0 days.

(21) Appl. No.: 10/306,874

(22) Filed: Nov. 27, 2002

(65) Prior Publication Data

US 2003/0144367 A1    Jul. 31, 2003

Related U.S. Application Data

(63) Continuation of application No. PCT/IB01/01011, filed on Jun. 11, 2001.

(60) Provisional application No. 60/215,489, filed on Jun. 30, 2000, provisional application No. 60/210,986, filed on Jun. 12, 2000.

(51) Int. Cl.
*B01J 23/56* (2006.01)
(52) U.S. Cl. .................................... 502/332
(58) Field of Classification Search ................ 502/260, 502/261, 262, 327, 328, 332, 333, 334, 339, 502/350, 351, 355, 340, 341, 415, 439
See application file for complete search history.

(56) References Cited

U.S. PATENT DOCUMENTS 4,120,826 A * 10/1978 Ebel et al. ................ 252/465
4,402,865 A * 9/1983 Blakely ..................... 252/432
5,733,839 A    3/1998 Espinoza et al. .......... 502/336
5,817,595 A * 10/1998 Tejada et al. .............. 502/313
5,856,365 A    1/1999 Zennaro et al. ........... 518/715
6,080,699 A * 6/2000 Pohl ......................... 502/303
6,130,184 A * 10/2000 Geerlings et al. .......... 502/350
6,262,132 B1 * 7/2001 Singleton et al. ......... 518/715
6,455,462 B2 * 9/2002 Van Berge et al. ......... 502/325

FOREIGN PATENT DOCUMENTS

EP    0681868          11/1995
WO    99/42214         8/1999
WO    0020116          4/2000
WO    01/39882 A1      6/2001

OTHER PUBLICATIONS

Knözinger, H. and P. Ratnasamy. "Catalytic Aluminas: Surface Models and Characterization of Surface Sites", *Catal. Rev. -Sci. Eng.*, (1978), 17(1): 31-70. Presented at the Fifth North American Meeting of the Catalysis Society, Pittsburgh, 1977.

* cited by examiner

*Primary Examiner*—Edward M. Johnson
(74) *Attorney, Agent, or Firm*—Ladas & Parry LLP

(57) ABSTRACT

A process for preparing a cobalt based catalyst precursor includes in a first support impregnation/drying/calcination stage, impregnating a particulate porous catalyst support with a cobalt salt, partially drying the impregnated support, and calcining the partially dried impregnated support to obtain a calcined material. The calcined material is partially reduced. Thereafter, in a second support impregnation/drying/calcination stage, the partially reduced material is impregnated with a cobalt salt, partially dried and calcined, to obtain the cobalt based catalyst precursor.

16 Claims, 1 Drawing Sheet

COBALT CATALYSTS

This application is a continuation of PCT/IB01/01011, field on Jun. 11, 2001, which claims priority to provisional applications 60/210,986, filed on Jun. 12, 2000, and 60/215,489, filed on Jun. 30, 2000.

THIS INVENTION relates to cobalt catalysts. In particular, the invention relates to a process for preparing a precursor of a cobalt based Fischer-Tropsch catalyst, to a process for preparing such a cobalt catalyst, and to a process for producing hydrocarbons using such a-cobalt catalyst.

The Applicant is aware of known processes for preparing cobalt based catalyst precursors and which involve slurry phase impregnation of a catalyst support with a cobalt salt, drying of the impregnated catalyst support, and calcination of the dried impregnated catalyst support, to achieve a desired cobalt loading of the support. The resultant precursors are then activated by reduction thereof, to obtain cobalt based Fischer-Tropsch catalysts. These catalysts can display good intrinsic activities when used for Fischer-Tropsch synthesis; however, catalysts having enhanced or superior intrinsic activities cannot readily be obtained using the known processes. It is thus an object of the present invention to provide a cobalt based Fischer-Tropsch catalyst having enhanced initial and/or stabilized intrinsic Fischer-Tropsch synthesis activity, as well as a process for preparing such a catalyst.

According to a first aspect of the invention, there is provided a process for preparing a cobalt based catalyst precursor, which process includes
in a first support impregnation/drying/calcination stage, impregnating a particulate porous catalyst support with a cobalt salt, partially drying the impregnated support, and calcining the partially dried impregnated support to obtain a calcined material;
partially reducing the calcined material; and
in a second support impregnation/drying/calcination stage, impregnating the partially reduced material with a cobalt salt, partially drying the impregnated material, and calcining the partially dried impregnated material, to obtain the cobalt based catalyst precursor.

The resultant cobalt catalyst precursor can then be reduced to obtain a cobalt based Fischer-Tropsch catalyst. It was surprisingly found that this catalyst has enhanced or superior initial as well as stabilized intrinsic Fischer-Tropsch synthesis activity.

Thus, according to a second aspect of the invention, there is provided a process for preparing a cobalt based Fischer-Tropsch catalyst, which process includes
in a first support impregnation/drying calcination stage, impregnating a particulate porous catalyst support with a cobalt salt, partially drying the impregnated support, and calcining the partially dried impregnated support to obtain a calcined material;
partially reducing the calcined material;
in a second support impregnation/drying/calcination stage, impregnating the partially reduced material with a cobalt salt, partially drying the impregnated material, and calcining the partially dried impregnated material, to obtain a cobalt based catalyst precursor; and
reducing the cobalt based catalyst precursor, to obtain the cobalt based Fischer-Tropsch catalyst.

In this specification, unless explicitly otherwise stated, where reference is made to catalyst mass, the mass given pertains to the calcined catalyst mass, ie the catalyst mass before any reduction of the catalyst is effective.

In the partial reduction of the calcined material, cobalt oxide present in the calcined material, ie a starting cobalt oxide phase, is partially reduced to a cobalt oxide phase containing less oxygen than the starting cobalt oxide phase. Without wishing to be bound thereby, it is believed that this phase containing the lower level of oxygen than the starting cobalt oxide phase, is a CoO like phase. Within the ambit of this specification, when reference is made to a CoO phase, it is thus intended that this means the partially reduced cobalt oxide phase.

A successful partial reduction of the calcined material may be assessed by performing X-ray diffraction analyses or by carrying out Temperature Programmed Reduction experiments on the calcined material.

The partial reduction of the calcined material may be performed at a temperature between a minimum temperature which is determined by the lowest temperature at which the partial reduction of the starting cobalt oxide phase to the CoO phase starts, and at a maximum temperature which is determined by the lowest temperature at which reduction of the CoO phase to a metallic cobalt phase starts. The minimum temperature may thus be 100° C., preferably 130° C., while the maximum temperature may be 300° C., preferably 250° C.

The partial reduction of the calcined material may be effected by contacting the calcined material with a hydrogen and/or carbon monoxide containing gas as a reducing gas, with an outlet gas being produced.

After completion of the partial reduction, which thus takes place in a partial reduction stage or vessel, the CoO phase may be unloaded into an inert atmosphere at the partial reduction temperature. Instead, however, it may be unloaded in air after first cooling down, or being cooled down, from the partial reduction temperature to room temperature. The CoO phase is stable in air at room temperature.

The partial reduction stage may be provided by any suitable contacting configuration of the calcined material with the reducing gas, such as a fluidized bed of the calcined material particles, with the reducing gas acting as the fluidizing medium; a fixed bed of the calcined material particles through which the reducing gas passes; or the like.

The cobalt salt may, in particular, be cobalt nitrate, $Co(NO_3)_2 \cdot 6H_2O$.

The particulate porous modified catalyst support may be any commercial available porous oxidic catalyst support, such as alumina ($Al_2O_3$), silica ($SiO_2$), a silica-alumina ($SiO_4 \cdot Al_2O_3$), titania ($TiO_2$) and magnesia (MgO).

The support may be a protected modified catalyst support containing, for example, silicon as a modifying component, as described in WO 99/42214 and which is hence incorporated herein by reference.

The support impregnation as well as the impregnation of the partially reduced material may, in principle, be effected by any suitable known impregnation method, eg incipient wetness impregnation, or slurry phase impregnation. Similarly, the calcination of the impregnated support as well as the calcination of the partially reduced material that was impregnated may be performed in any suitable known calcination unit, eg in a fluidized bed, in a fixed bed, in a furnace, in a rotary kiln, and/or in a torbed calciner, preferably at temperatures between 150° C. and 300° C. In particular, the calcination may be in-accordance with that described in PCT/IB00/01745, and which is thus incorporated herein by reference. The calcination may thus involve fluidized bed calcination as described in PCT/IB00/01745.

The support and partially reduced material impregnation, drying and calcination may, in particular, be in accordance with the process described in our copending WO 00/20116, which is thus incorporated herein by reference. The precursor preparation may thus involve a 2-step slurry phase impregnation, partial drying and calcination process as described in WO 00/20116, which is dependant on a desired active component (cobalt) loading requirement and the pore volume of the porous oxidic catalyst support.

The support impregnation and drying may typically be effected in a conical vacuum drier with a rotating screw or in a tumbling vacuum drier.

The catalyst precursor may contain between 5 gCo/100 g support and 70 g Co/100 g support, preferably between 20 gCo/100 g support and 50 g Co/100 g support.

During either or both of the impregnation stages, a water soluble precursor salt of palladium (Pd) or platinum (Pt) or a mixture of such salts may be added, as a dopant capable of enhancing the reducibility of the cobalt.

Preferably, the dopant is added in a mass proportion of the palladium metal, the platinum metal or the mixture of palladium and platinum metals to the cobalt metal of between 0,01:100 to 0,3:100.

The invention extends also to a cobalt based Fischer-Tropsch catalyst, when produced by the process of the second aspect of the invention, and to a cobalt based catalyst precursor, when produced by the process of the first aspect of the invention.

According to a third aspect of the invention, there is provided a process for producing hydrocarbons, which includes contacting synthesis gas comprising hydrogen ($H_2$) and carbon monoxide (CO) at an elevated temperature between 180° C. and 250° C. and an elevated pressure between 1 and 40 bar with a cobalt catalyst according to the invention, in a slurry phase Fischer-Tropsch reaction of the hydrogen with the carbon monoxide, to obtain hydrocarbons.

The invention extends also to hydrocarbons when produced by the process as hereinbefore described.

The invention will now be described in more detail with reference to the following non-limiting examples and with reference to the drawings.

IN THE DRAWINGS

EXAMPLE 1

Figure 1:
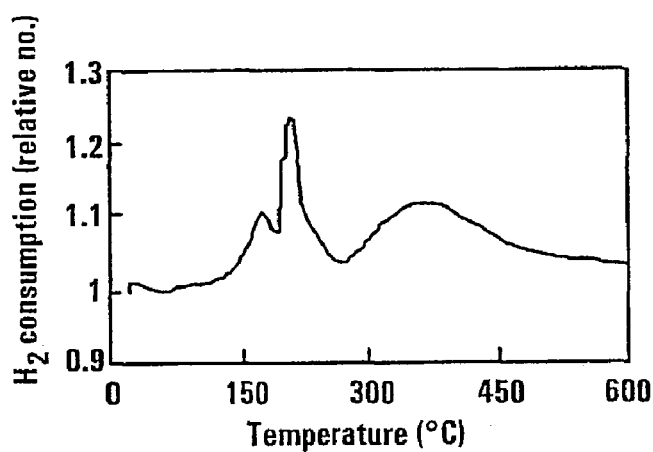
FIG. 1 shows the temperature programmed reduction (TPR) pattern of catalyst G, after the $1^{st}$ impregnation/drying and calcination stage.

Catalyst B [(30 g Co/100 g $Al_2O_3$)] (30 g Co/0.075 g Pt/100 g $Al_2O_3$) (Not in Accordance with the Invention)

Preparation

A Pt promoted catalyst was prepared on SASOL Germany GmbH's trademark product: Puralox SCCa 5/150, as a selected pre-shaped $Al_2O_3$ support, in accordance with the method of aqueous slurry phase impregnation and vacuum drying, followed by direct fluidized bed calcination, in accordance with Catalyst Example 1 of WO 00/20116, or one of Catalysts D, E, G or H of PCT/IB00/01745.

In preparation for laboratory scale slurry phase continuous stirred tank reactor ('CSTR') Fischer-Tropsch synthesis runs, this calcined material was reduced and wax coated in accordance with the following procedure:

27.5 g of the catalyst was reduced at 1 bar pure $H_2$ (space velocity≧200 mln $H_2$/g catalyst/h) whilst the temperature was increased from 25° C. to 380° C.-425° C. at a rate of 1° C./min whereafter the temperature was kept constant at this temperature of 380° C.-425° C. for 16 hours.

The reduced catalyst was allowed to cool down to room temperature at which stage the hydrogen was replaced by argon, and the catalyst unloaded in molten Fischer-Tropsch wax under the protection of an argon blanket. This wax coated catalyst was then transferred to the slurry reactor.

CSTR Fischer-Tropsch Synthesis Run

An extended slurry phase CSTR Fischer-Tropsch synthesis run (number 106F) was performed on catalyst B. This run lasted about ('ca') 90 days, during which the following synthesis conditions were maintained:

| | |
|---|---|
| Reactor temperature | 220.5° C. |
| Reactor pressure | 20.3 bar |
| Catalyst inventory | 20.8 g |
| ($H_2$ + CO) space velocity | 2169 $ml_n$/(g catalyst · h) |
| APG space velocity | 2452 $ml_n$/(g catalyst · h), | where 'APG' is an acronym for Arge Pure Gas, ie the commercial synthesis gas produced at Schümann-Sasol (Pty) Limited in Sasolburg, South Africa, according to the method of coal gasification, followed by Rectisol (trademark) purification.

| Feed gas composition: | |
|---|---|
| $H_2$ | 49.1 vol % |
| CO | 25.9 vol % |
| $CH_4$ | 9.3 vol % |
| $CO_2$ | 0.5 vol % |
| Ar | 15.2 vol % |

The observed synthesis performance data of this run (ie 106F) is presented in Table 1.

Relative (Fischer-Tropsch) Intrinsic Activity Factor ('R.I.A.F.') is defined as follows:

Consider an arbitrary slurry phase cobalt Fischer-Tropsch catalyst, displaying the following observed synthesis performance in a CSTR:

$r_{FT}$=Z moles CO converted to Fischer-Tropsch products per gram catalyst per second, observed at T=γ Kelvin, at the following set of reactor partial pressures:

$P_{H2}$=ν bar $P_{CO}$=τ bar then the definition of R.I.A.F. is as follows:

$$R.I.A.F=[Z(1+1.82\tau)^2]/[49480.9e^{(-11113.4/\gamma)}\nu\tau]$$

Initial intrinsic Fischer-Tropsch activity ($a_i$) of a slurry phase cobalt based catalyst is defined as follows:

$a_i$=the R.I.A.F. after 15 hours on stream (ie $t_i$=time initial) of continuous exposure to the following set of gradientless slurry phase synthesis conditions:

220° C., 20 bar, % ($H_2$+CO) conversion in excess of 50%, obtained with a feed gas of composition: ca 50 vol % $H_2$ and ca 25 vol % CO, the balance consisting of Ar, $N_2$, $CH_4$ and/or $CO_2$.

EXAMPLE 2

Example of $Al_2O_3$ Supported Cobalt Slurry Phase Catalyst in Accordance with the Invention (Catalyst G) that Displayed Enhanced Initial Intrinsic Fischer-Tropsch Activities Catalyst G (30 gCo/0,075 gPt/100 g$Al_2O_3$) A Pt promoted cobalt catalyst was prepared on SASOL Germany GmbH's trademark product: Puralox SCCa 5/150 as the selected pre-shaped support material, in accordance with the method of aqueous slurry phase impregnation and vacuum drying, followed by direct fluidized bed calcination disclosed in U.S. Pat. No. 5,733,839, WO 99/42214 and WO 00/20116. In particular, the catalyst was prepared as follows:

44.6 g $Co(NO_3)_2 \cdot 6H_2O$ was dissolved in 40 ml distilled water and 0.0248 g $(NH_3)_4Pt(NO_3)_2$ was dissolved in 10 ml distilled water. These two solutions were mixed together in a 500 ml round ball flask in a rotavapor at 60° C. and atmospheric pressure, and 50 g of the Puralox SCCa 5/150 support material was added. Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 240 | 30 |
| 70 | 244 | 90 |
| 85 | 242 | 60 |
| 85 | 50 | 240 |

This vacuum dried intermediate product was directly subjected to a fluidized bed calcination step according to the following procedure:

Continuous air flow of 1.7 $dm^3_n$/min

Temperature program:

$$25°C. \xrightarrow{1°C./min} 250°C. \xrightarrow{6\ hours} 250°C.$$

This calcined intermediate product of the $1^{st}$ cobalt/platinum impregnation and calcination step was then subjected to a partial reduction step prior to the $2^{nd}$ (and last) cobalt/platinum impregnation step. For this purpose this intermediate material was reduced at 1 bar pure hydrogen (space velocity of 2000 $ml_n$/g intermediate.h) whilst the temperature was increased from 25° C. to 230° C. at a rate of 1° C./min whereafter the temperature was kept constant at 230° C. for 2 hours.

35.0 g of this partially reduced intermediate material was transferred to the aqueous impregnation solution of the $2^{nd}$ cobalt/platinum impregnation step under the protection of an argon blanket, an impregnation solution that was prepared as follows:

22.7 g $Co(NO_3)_2 \cdot 6H_2O$ was dissolved in 28 ml distilled water and 0.0401 g $(NH_3)_4Pt(NO_3)_2$ was dissolved in 7 ml distilled water. These two solutions were mixed together in a 500 ml round ball flask in a rotavapor at 60° C. and atmospheric pressure.

Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 300 | 30 |
| 70 | 307 | 90 |
| 85 | 301 | 60 |
| 85 | 50 | 240 |

This vacuum dried intermediate product was directly subjected to a fluidized bed calcination step, according to the following procedure:

Continuous air flow of 1.7 $dm^3_n$/min

Temperature program:

$$25°C. \xrightarrow{1°C./min} 250°C. \xrightarrow{6\ hours} 250°C.$$

Figure 2:
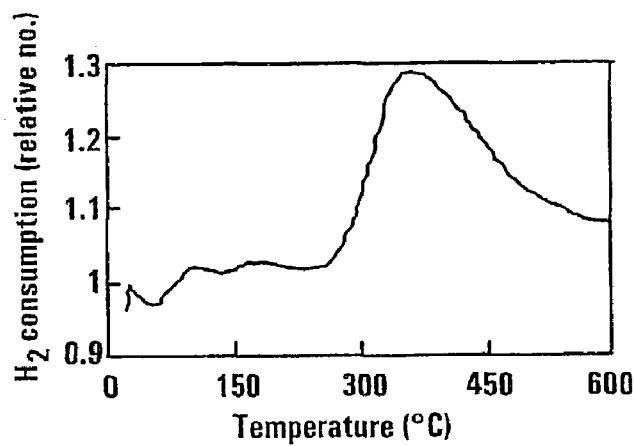
FIG. 2 shows the TPR pattern of catalyst G, after the partial reduction stage.
Figure 3:
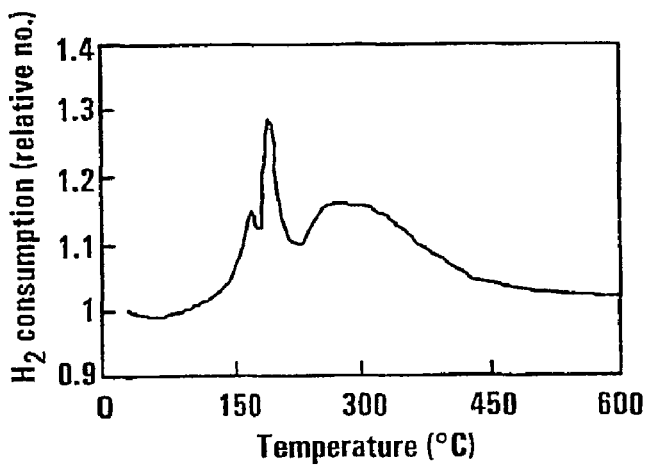
FIG. 3 shows the TPR pattern of catalyst G, after the second and final impregnation/drying and calcination stage.

Temperature programmed reduction experiments were performed on the catalyst intermediates after $1^{st}$ impregnation and calcination step, after the partial reduction as well as after the $2^{nd}$ impregnation and calcination step. It can be seen in FIG. 1 that the TPR pattern of the catalyst intermediate after $1^{st}$ impregnation and calcination shows several reduction steps. The first two reduction peaks are probably the reduction to CoO and the last broad peak the reduction of CoO to metallic cobalt The TPR pattern of the catalyst sample after the partial reduction step (ie FIG. 2) shows only the broad reduction peak of the reduction of CoO to metallic cobalt. The partial reduction thus caused the reduction of cobalt oxides to CoO. The TPR pattern of the catalyst intermediate after $2^{nd}$ impregnation and calcination (ie FIG. 3) again shows several reduction peaks, similar to the TPR pattern of the sample after $1^{st}$ impregnation and calcination.

In preparation for laboratory scale slurry phase CSTR Fischer-Tropsch synthesis runs, the finally calcined catalyst precursor was reduced and wax coated in accordance with the procedure described for the preparation of catalyst B.

Catalyst G was tested for its Fischer-Tropsch performance in a similar manner as described in example 1. The observed results are presented in Table 1.

TABLE 1

| Catalyst | B (comparative) | G (in accordance with the invention) |
|---|---|---|
| Catalyst characteristics: | | |
| Composition | 30 g Co/0.075 g Pt/100 g $Al_2O_3$ | 30 g Co/0.075 g Pt/100 g $Al_2O_3$ |
| Synthesis performance data: | | |
| Run analysis number | 106F | 46£1 |
| Time on stream (hours) | 15 | 15 |
| % ($H_2$ + CO) conversion | 73 | 65 |
| Reactor partial pressures: | | |
| $H_2$ (bar) | 3.7 | 5.0 |
| CO (bar) | 2.4 | 2.9 |
| $H_2O$ (bar) | 5.0 | 4.4 |
| $CO_2$ (bar) | 0.3 | 0.3 |
| Initial Relative Intrinsic (Fischer-Tropsch) Activity Factor (i.e.: $a_i$ = R.I.A.F. at $t_i$) | 2.7 | 4.7 |

The following conclusion can be drawn from Table 1:

Catalyst G, ie 30 gCo/0.075 gPt/100 gAl$_2$O$_3$ prepared by using a partial reduction step as an additional preparation step, displayed an initial RIAF of 4,7, which is about 70% higher than the initial RIAF of 2,8 of catalyst B, ie 30 gCo/0.075 gPt/100 gAl$_2$O$_3$ prepared without a partial reduction step.

In this invention it was thus surprisingly found that cobalt based Fischer-Tropsch synthesis catalysts displayed an increased intrinsic catalytic performance when these catalysts were prepared using a partial reduction step as an additional preparation step prior to the final impregnation/drying and calcination step, eg the partial reduction step was performed in between the 1$^{st}$ and 2$^{nd}$ impregnation/drying/calcination steps.

The invention claimed is:

1. A process for preparing a cobalt based catalyst precursor, which process includes in a first support impregnation/drying/calcination stage, impregnating a particulate porous catalyst support with a cobalt salt, partially drying the impregnated support, and calcining the partially dried impregnated support to obtain a calcined material having a starting cobalt oxide phase;

partially reducing the calcined material at a temperature of from 100° C. to 300° C., so that the starting cobalt oxide phase is partially reduced to a cobalt oxide phase containing less oxygen than the starting cobalt oxide phase, thereby to obtain a partially reduced material; and in a second support impregnation/drying/calcination stage, impregnating the partially reduced material with a cobalt salt, partially drying the impregnated material, and calcining the partially dried impregnated material, to obtain the cobalt based catalyst precursor.

2. A process according to claim 1, wherein the cobalt salt used in both impregnation/drying/calcination stages is cobalt nitrate, and wherein the porous catalyst support is alumina, silica, a silica-alumina, titania or magnesia.

3. A process according to claim 1, wherein the support is a protected modified catalyst support containing silicon as a modifying component.

4. A process according to claim 1, wherein the cobalt based catalyst precursor contains between 5 g Co/100 g support and 70 g Co/100 g support.

5. A process according to claim 1, wherein during either or both of the impregnation stages, a water soluble precursor salt of palladium (Pd), platinum (Pt) or a mixture thereof is added, as a dopant capable of enhancing the reducibility of the cobalt.

6. A process according to claim 1, wherein the partial reduction of the calcined material is effected by contacting the calcined material with a hydrogen and/or carbon monoxide containing gas.

7. A process according to claim 1, wherein the partial reduction of the calcined material is at a temperature that does not result in a reduction to a metallic cobalt phase of the cobalt oxide phase containing less oxygen.

8. A process according to claim 1, wherein the cobalt oxide phase containing less oxygen formed by the partial reduction is stable in air at room temperature.

9. A process for preparing a cobalt based Fischer-Tropsch catalyst, which process includes in a first support impregnation/drying/calcination stage, impregnating a particulate porous catalyst support with a cobalt salt, partially drying the impregnated support, and calcining the partially dried impregnated support to obtain a calcined material having a starting cobalt oxide phase;

partially reducing the calcined material at a temperature of from 100° C. to 300° C., so that the starting cobalt oxide phase is partially reduced to a cobalt oxide phase containing less oxygen than the starting cobalt oxide phase, thereby to obtain a partially reduced material;

in a second support impregnation/drying/calcination stage, impregnating the partially reduced material with a cobalt salt, partially drying the impregnated material, and calcining the partially dried impregnated material, to obtain a cobalt based catalyst precursor; and reducing the cobalt based catalyst precursor, to obtain the cobalt based Fischer-Tropsch catalyst.

10. A process according to claim 9, wherein the cobalt salt used in both impregnation/drying/calcinations stages is cobalt nitrate, and wherein the porous catalyst support is alumina, silica, a silica-alumina, titania or magnesia.

11. A process according to claim 9, wherein the support is a protected modified catalyst support containing silicon as a modifying component.

12. A process according to claim 9, wherein the cobalt based catalyst precursor contains between 5 gCo/100 g support and 70gCo/100g support.

13. A process according to claim 9, wherein during either or both of the impregnation stages, a water soluble precursor salt of palladium (Pd), platinum (Pt) or a mixture thereof is added, as a dopant capable of enhancing the reducibility of the cobalt.

14. A process according to claim 9, wherein the partial reduction of the calcined material is effected by contacting the calcined material with a hydrogen and/or carbon monoxide containing gas.

15. A process according to claim 9, wherein the partial reduction of the calcined material is at a temperature that does not result in a reduction to a metallic cobalt phase of the cobalt oxide phase containing less oxygen.

16. A process according to claim 9, wherein the cobalt oxide phase containing less oxygen formed by the partial reduction is stable in air at room temperature.

* * * * *